(12) United States Patent
Proksa et al.

(10) Patent No.: US 10,143,434 B2
(45) Date of Patent: Dec. 4, 2018

(54) IMAGING SYSTEM FOR GENERATING AN IMAGE OF AN OBJECT

(71) Applicant: KONINKLIJKE PHILIPS N.V., Eindhoven (NL)

(72) Inventors: Roland Proksa, Neu Wulmstorf (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 119 days.

(21) Appl. No.: 15/312,372

(22) PCT Filed: May 13, 2015

(86) PCT No.: PCT/EP2015/060679
§ 371 (c)(1),
(2) Date: Nov. 18, 2016

(87) PCT Pub. No.: WO2015/185343
PCT Pub. Date: Dec. 10, 2015

(65) Prior Publication Data
US 2017/0079605 A1 Mar. 23, 2017

(30) Foreign Application Priority Data

Jun. 4, 2014 (EP) ..................................... 14171093

(51) Int. Cl.
*A61B 6/00* (2006.01)
*G01T 1/36* (2006.01)
(Continued)

(52) U.S. Cl.
CPC ............ *A61B 6/5205* (2013.01); *A61B 6/032* (2013.01); *A61B 6/482* (2013.01); *G01T 1/2985* (2013.01); *G01T 1/36* (2013.01)

(58) Field of Classification Search
CPC ............................. A61B 6/4241; A61B 6/482
See application file for complete search history.

(56) References Cited

U.S. PATENT DOCUMENTS

2007/0147574 A1* 6/2007 Bernard De Man .. A61B 6/032
378/4
2013/0101156 A1* 4/2013 Holt ....................... G01N 23/06
382/103

OTHER PUBLICATIONS

Carmi, et al., "Material Separation with Dual-Layer CT", IEEE Nuclear Science Symposium Conference Record, vol. 4, pp. 1876 to 1878 (2005).

(Continued)

*Primary Examiner* — Dani Fox

(57) ABSTRACT

The invention relates to an imaging system (17) like a computed tomography system for generating an image of an object. Spectral measured projection data and non-spectral measured projection data are generated by a detector (6) having spectral detection elements and non-spectral detection elements, and spectral estimated projection data are estimated by using a model material distribution which could have caused the non-spectral measured projection data and by simulating a measurement of the spectral estimated projection data based on the model material distribution. An image is reconstructed based on the measured and estimated spectral projection data. Using the spectral estimated projection data in addition to the spectral measured projection data can lead to high quality spectral imaging, especially high quality spectral computed tomography imaging, which uses a simplified detector not only having generally more complex spectral detection elements, but also having simpler non-spectral detection elements.

20 Claims, 4 Drawing Sheets

(51) Int. Cl.
  *G01T 1/29* (2006.01)
  *A61B 6/03* (2006.01)

(56) References Cited

OTHER PUBLICATIONS

Roessl, et al., "K-edge imaging in x-ray computed tomography using multi-bin photon counting detectors", Physics in Medicine and Biology, vol. 52, pp. 4679 to 4696 (2007).
Altman, et al., "A Dual-Energy CT Based on a Double Layer Detector", 51st AAPM Annual Meeting, 2014.

* cited by examiner

IMAGING SYSTEM FOR GENERATING AN IMAGE OF AN OBJECT

CROSS REFERENCE TO RELATED APPLICATIONS

This application is the U.S. National Phase application under 35 U.S.C. § 371 of International Application No. PCT/EP2015/060679, filed May 13, 2015, published as WO 2015185343 on Dec. 10, 2015, which claims the benefit of European Patent Application Number 14171093.9 filed Jun. 4, 2014. These applications are hereby incorporated by reference herein.

FIELD OF THE INVENTION

The invention relates to an imaging system, an imaging method and an imaging computer program for generating an image of an object. The invention relates especially to a spectral computed tomography system, method and computer program for generating an image of an object.

BACKGROUND OF THE INVENTION

US 2007/0147574 A1 discloses a system for acquiring an image data set comprising energy integrating and energy discriminating data measurements. The system is adapted to obtain energy integrating measurement data and energy discriminating measurement data during an acquisition cycle and to combine and reconstruct the energy integrating measurement data and the energy discriminating measurement data in a selected manner to generate an energy discriminating component image.

US 2013/0101156 A1 discloses an apparatus comprising a non-invasive imaging device having at least one modality with at least one spectral channel. The apparatus further comprises a memory having stored therein a plurality of models for different materials and feasibility criteria and a control circuit being configured to process imaging information for an object as provided by the non-invasive imaging device, wherein the plurality of models are used to identify candidate materials for portions of the imaging information and wherein the feasibility criteria are used to reduce the candidate materials by avoiding unlikely materials or combinations of materials.

The article "Material Separation with Dual-Layer CT" by R. Carmi et al., IEEE Nuclear Science Symposium Conference Record, volume 4, pages 1876 to 1878 (2005) discloses a spectral computed tomography system using a dual layer detector for generating spectral projection data and a reconstruction unit for reconstructing an image of an object like a person based on the generated spectral projection data. The dual layer detector uses a technically complex configuration with two sensitive detection layers in a stack, in order to provide energy separation.

SUMMARY OF THE INVENTION

It is an object of the present invention to provide an imaging system, method and computer program for imaging an object, which allow for the generation of an image of the object based on spectral projection data, wherein a technically less complex detector can be used.

In a first aspect of the present invention an imaging system for generating an image of an object is presented, wherein the imaging system comprises:

a measured projection data providing unit for providing spectral measured projection data and non-spectral measured projection data, wherein the spectral measured projection data and the non-spectral measured projection data have been generated by a detector having spectral detection elements and non-spectral detection elements, respectively, based on radiation having traversed an imaging region which includes the object, an estimation unit for estimating spectral estimated projection data, which correspond to radiation paths ending at the non-spectral detection elements, wherein for estimating a spectral estimated projection data value for a radiation path ending at a non-spectral detection element the estimation unit is adapted to a) determine a model material distribution within the imaging region, which could have caused a non-spectral measured projection data value that corresponds to the radiation path, based on the non-spectral measured projection data and b) simulate a measurement of the spectral estimated projection data value based on the model material distribution, a reconstruction unit for reconstructing an image of the object based on the spectral measured projection data and the spectral estimated projection data.

Since the imaging system can generate the image of the object based on provided spectral measured projection data and non-spectral measured projection data, the detector used for generating theses measured projection data does not need to comprise spectral detection elements only, which are technically more complex than non-spectral detection elements, thereby reducing the overall technical complexity of the detector. Moreover, since the estimation unit can estimate spectral estimated projection data which correspond to radiation paths ending at the non-spectral detection elements, wherein these spectral estimated projection data are used together with the provided spectral measured projection data for reconstructing the image of the object, a high quality image of the object can still be generated. For instance, since the detector does not only comprise spectral detection elements, the spectral measured projection data are likely truncated, which can lead to image artifacts in the generated image. This truncation and the corresponding image artifacts can be mitigated, especially eliminated, by not only using the spectral measured projection data for reconstructing the image, but by also using the spectral estimated projection data.

The measured projection data providing unit can be a projection data acquisition system for acquiring the spectral measured projection data and the non-spectral measured projection data by using a detector having spectral detection elements and non-spectral detection elements. However, the measured projection data providing unit can also be just a storing unit for storing the spectral measured projection data and the non-spectral measured projection data and for retrieving the stored spectral measured projection data and non-spectral measured projection data for providing the same. The measured projection data providing unit can also be a receiving unit for receiving the spectral measured projection data and non-spectral measured projection data from a projection data acquisition system and for providing the received spectral measured projection data and non-spectral measured projection data.

The object is preferably a living object like a person or an animal. However, the object can also be a technical object. For instance, the imaging system can be used for generating images of luggage at an airport for security reasons.

In a preferred embodiment, for determining the model material distribution for estimating a spectral estimated projection data value the estimation unit is adapted to determine a model material distribution along a radiation path that corresponds to the spectral estimated projection data value to be determined based on a corresponding non-spectral projection data value. In particular, the estimation unit is adapted to estimate a water distribution as the model material distribution along the radiation path. For instance, for a non-spectral measured projection data value an equivalent water length can be determined based on the respective non-spectral measured projection data value. The equivalent water length can then be used to determine the spectral estimated projection data value by simulating a travelling of the radiation along the equivalent water length. This allows for a relatively fast estimation of spectral estimated projection data based on the non-spectral measured projection data and the projection data generation parameters.

The simulation of a measurement of the spectral estimated projection data value is preferentially a simulation simulating a measurement which uses a kind of detector element which has also been used for measuring the spectral measured projection data. Thus, it preferentially considers the detection technology used for measuring the spectral measured projection data. For instance, if the detector elements used for measuring the spectral measured projection data are dual layer detector elements having two sensitive detection layers in a stack, in order to provide photon energy separation, known absorption characteristics of the layers are preferentially considered while simulating the measurement process.

In a further embodiment, for determining the model material distribution for estimating a spectral estimated projection data value the estimation unit is adapted to reconstruct an intermediate image based on the spectral measured projection data and the non-spectral projection data and to determine the material distribution based on the reconstructed intermediate image. In particular, the estimation unit is adapted to integrate the spectral measured projection data, thereby generating integrated projection data, and to reconstruct the intermediate image based on the integrated projection data and the non-spectral measured projection data. Preferentially, the estimation unit is adapted to determine the material distribution by segmenting different materials in the reconstructed intermediate image. For instance, if the object is a person, bone and tissue areas can be segmented in the reconstructed intermediate image and this segmentation can be used to determine a distribution of calcium and water along a respective radiation path, wherein this calcium/water material distribution can be used to simulate a measurement of a spectral estimated projection data value for determining the same. This allows for a further improved accuracy of estimating spectral estimated projection data.

It is also preferred that the estimation unit is adapted to smooth the spectral measured and estimated projection data at a boundary between the spectral measured projection data and the spectral estimated projection data. The transition from the spectral measured projection data to the spectral estimated projection data may not be very smooth. By smoothing these projection data at this transition or boundary the quality of the finally reconstructed image of the object may be further improved.

In a further aspect of the present invention an imaging method for generating an image of an object is presented, wherein the imaging method comprises:

providing spectral measured projection data and non-spectral measured projection data by a measured projection data providing unit, wherein the spectral measured projection data and the non-spectral measured projection data have been generated by a detector having spectral detection elements and non-spectral detection elements, respectively, based on radiation having traversed an imaging region including the object, estimating spectral estimated projection data, which correspond to radiation paths ending at the non-spectral detection elements, by an estimation unit, wherein for estimating a spectral estimated projection data value for a radiation path ending at a non-spectral detection element the estimation unit a) determines a model material distribution within the imaging region, which could have caused a non-spectral measured projection data value that corresponds to the radiation path, based on the non-spectral measured projection data and b) simulates a measurement of the spectral estimated projection data value based on the model material distribution, reconstructing an image of the object based on the spectral measured projection data and the spectral estimated projection data by a reconstruction unit.

In a further aspect of the present invention a computer program for imaging a region of interest is presented, wherein the computer program comprises program code means for causing an imaging system as defined in claim 1 to carry out the steps of the imaging method as defined in claim 9, when the computer program is run on a computer controlling the imaging system.

It shall be understood that the imaging system of claim 1, the imaging method of claim 9 and the computer program of claim 10 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
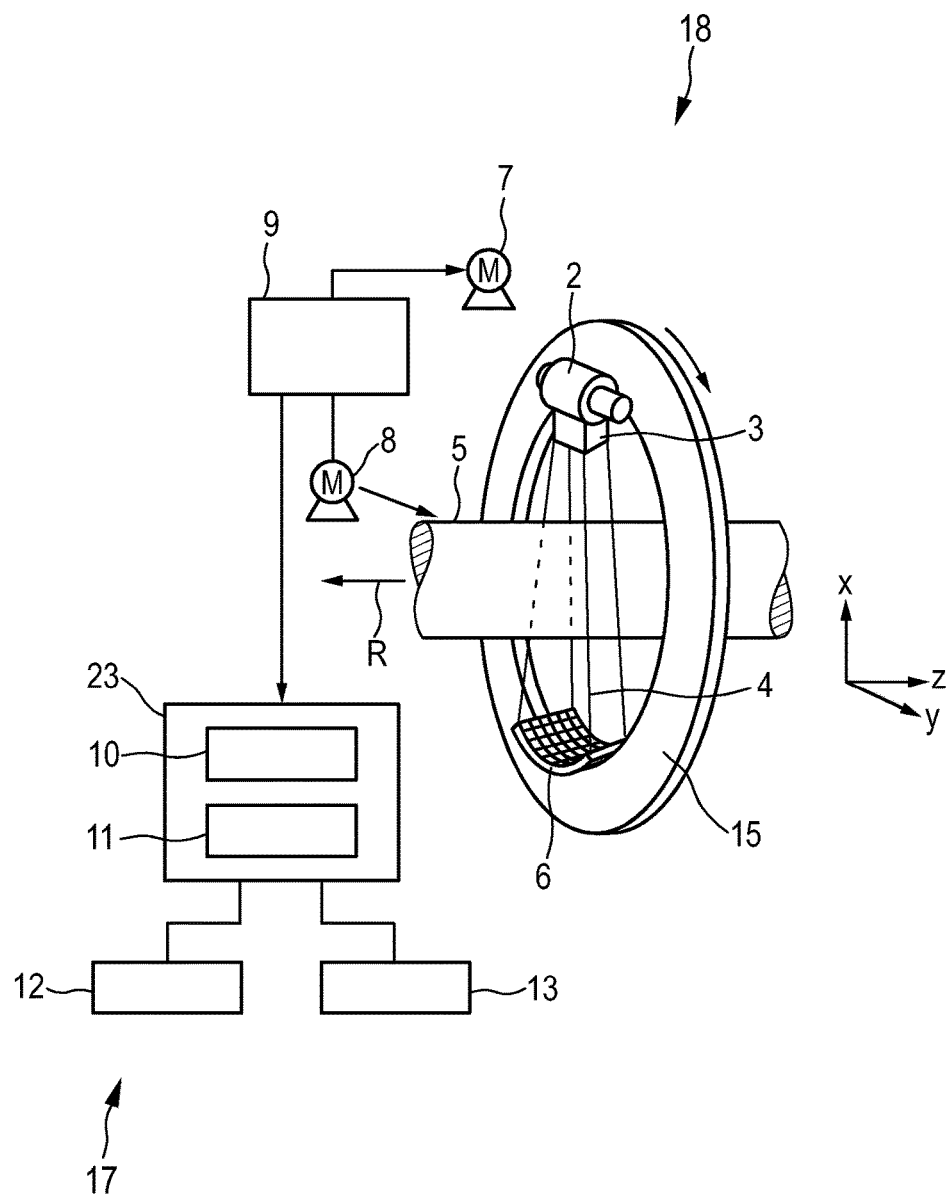
FIG. 1 schematically and exemplarily shows an embodiment of an imaging system for generating an image of an object, FIG. 2 schematically and exemplarily shows a detector with spectral detection elements and non-spectral detection elements, FIG. 3 schematically and exemplarily illustrates truncated spectral measured projection data and spectral estimated projection data.

FIG. 1 shows schematically and exemplarily an embodiment of an imaging system for generating an image of an object. In this embodiment the imaging system 17 is a spectral computed tomography system for generating a computed tomography image of a person. The computed tomography system 17 includes a gantry 1 which is capable of rotation about a rotational axis R which extends parallel to a z direction. A radiation source 2, which is, in this embodiment, an x-ray tube, is mounted on the gantry 1. The radiation source 2 is provided with a collimator 3, which forms, in this embodiment, a conical radiation beam 4 from the radiation generated by the radiation source 2. The radiation traverses the person (not shown in FIG. 1) within an imaging region 5, which may also be regarded as being an examination zone and which is, in this embodiment, cylindrical. After having traversed the imaging region 5, the radiation beam 4 is incident on a detector 6 comprising a two-dimensional detection surface. The detector 6 is mounted on the gantry 1.

The computed tomography system 17 comprises two motors 7, 8. The gantry 1 is driven at a preferably constant but adjustable angular speed by the motor 7. The motor 8 is provided for displacing the person, who is arranged on a support means like a table within the imaging region 5, parallel to the direction of the rotational axis R or the z axis. These motors 7, 8 are controlled by a control unit 9, for instance, such that the radiation source 2 and the person move relatively to each other along a helical trajectory. However, it is also possible that the person is not moved, but that only the radiation source 2 is rotated, i.e. that the radiation source 2 moves along a circular trajectory relative to the person. Furthermore, in another embodiment the collimator 3 can be adapted for forming another beam shape, in particular a fan beam, and the detector 6 can comprise a detection surface, which is shaped corresponding to the other beam shape, in particular to the fan beam.

Figure 2:
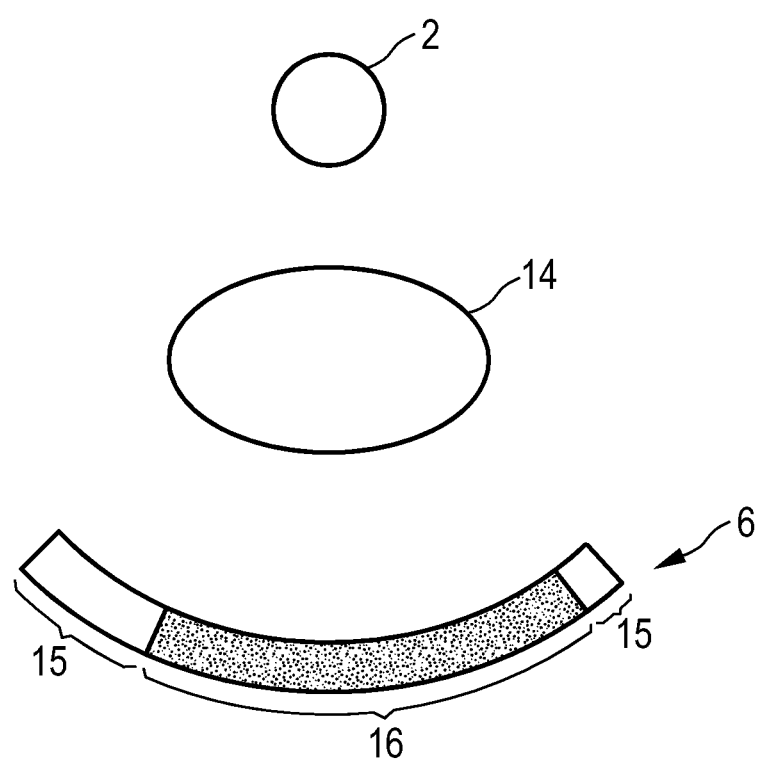

As schematically and exemplarily illustrated in FIG. 2, after the radiation emitted by the radiation source 2 has traversed the person 14, the radiation is detected by non-spectral detection elements 15 and spectral detection elements 16 of the detector 6. Thus, the detector 6 does not only comprise spectral detection elements 16, but also non-spectral detection elements 15. During a relative movement of the radiation source 2 and the person, the detector 6 generates spectral measured projection data by using the spectral detection elements 16 and non-spectral measured projection data by using the non-spectral detection elements 15 depending on the radiation incident on the detection surface of the detector 6. Therefore, the radiation source 2, the elements for moving the radiation source 2 relative to the person, in particular, the motors 7, 8 and the gantry 1, and the detector 6 form a measured projection data providing unit 18 for providing spectral measured projection data and non-spectral measured projection data, wherein the spectral measured projection data and the non-spectral measured projection data have been generated by the detector 6 with the spectral detection elements 16 and the non-spectral detection elements 15, respectively, based on the radiation 4 having traversed the imaging region 4 including the person 14 in accordance with projection data generation parameters describing the generation of the projection data. The measured projection data providing unit 18 can also be regarded as being a projection data acquisition system.

The projection data generation parameters describe the generation of the projection data, i.e. they describe, for instance, the acquisition geometry and the intensity of the radiation used for generating the spectral measured projection data and the non-spectral measured projection data. The acquisition geometry defines the radiation paths with respect to the object, along which the radiation has travelled before being detected by the spectral and non-spectral detection elements of the detector.

Figure 3:
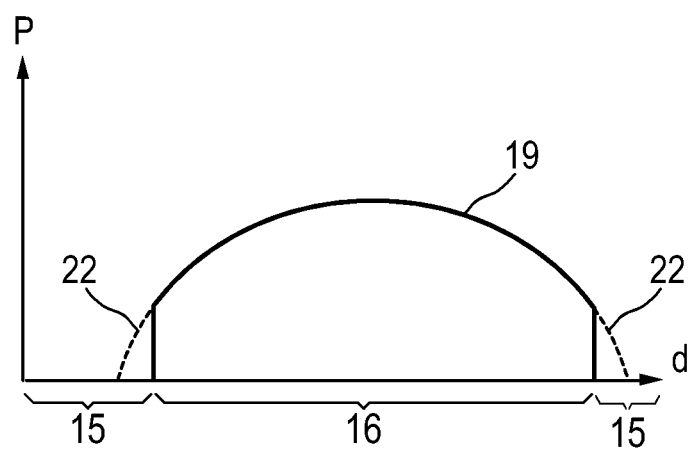

The spectral measured projection data 19 can be truncated as schematically and exemplarily illustrated in FIG. 3. FIG. 3 shows exemplarily and schematically spectral measured projection data values P depending on the respective detection elements d on the detector 6. As can be seen in FIG. 3, at the boundaries between the non-spectral detection elements 15 and the spectral detection elements 16 the spectral measured projection data 19 are truncated.

The computed tomography system 17 therefore further comprises an estimation unit 10 for estimating spectral estimated projection data 22, which correspond to radiation paths ending at the non-spectral detection elements 15, wherein for estimating a spectral estimated projection data value for a radiation path ending at a non-spectral detection element 15 the estimation unit 10 is adapted to a) determine a model material distribution within the imaging region 5, which could have caused a non-spectral measured projection data value that corresponds to the radiation path, based on the non-spectral measured projection data and optionally also based on the projection data generation parameters, and b) simulate a measurement of the spectral estimated projection data value based on the model material distribution and optionally also based on the projection data generation parameters. In particular, the estimation unit 10 is adapted to determine a model material distribution along a radiation path that corresponds to the spectral estimated projection data value to be determined based on a corresponding non-spectral projection data value and the projection data generation parameters. For instance, the estimation unit 10 is adapted to estimate a water distribution, i.e. an equivalent water length, as the model material distribution along the radiation path. Alternatively, the estimation unit 10 can be adapted to reconstruct an intermediate image based on the spectral measured projection data, the non-spectral projection data and the projection data generation parameters, and to determine the material distribution based on the reconstructed intermediate image. In this case the estimation unit 10 is preferentially adapted to integrate the spectral measured projection data, thereby generating integrated projection data, and to reconstruct the intermediate image based on the integrated projection data, the non-spectral measured projection data and the projection data generation parameters. The estimation unit 10 can be adapted to determine the material distribution by segmenting different materials in the reconstructed intermediate image. For instance, bone and tissue areas may be segmented in the reconstructed intermediate image, in order to determine the material distribution.

The estimation unit 10 is further adapted to smooth the spectral measured projection data 19 and the spectral estimated projection data 22 at the boundaries between the spectral detection elements 16 and the non-spectral detection elements 15. In FIG. 3 the smoothed spectral estimated projection data are indicated by the broken lines 22.

The computed tomography system 17 further comprises a reconstruction unit 11 for reconstructing the image of the person 14 based on the spectral measured projection data, the spectral estimated projection data and the projection data generation parameters. In this embodiment the reconstruction unit 11 is adapted to use a filtered back projection algorithm for reconstructing the image of the person. The reconstruction unit 11 can be adapted to use a material decomposition technique, in order to reconstruct different images, which correspond to different materials within the person, based on the spectral projection data. For instance, if a contrast agent has been injected into the person, a first image can be reconstructed only showing the contrast agent within the person and a second image can be reconstructed showing the person without the contrast agent. The reconstruction unit 11 can also be adapted to reconstruct different images, which correspond to different physical effects like the Compton effect and the photoelectric effect, based on the spectral projection data. The reconstruction unit 11 can of course also be adapted to use other spectral reconstruction techniques. Known reconstruction techniques, which might be used by the reconstruction unit, are disclosed, for instance, in the article "K-edge imaging in x-ray computed tomography using multi-bin photon counting detectors" by E. Roessl and R. Proksa, Physics in Medicine and Biology, volume 52, pages 4679 to 4696 (2007), which is herewith incorporated by reference.

The estimation unit 10 and the reconstruction unit 11 are parts of an image generation device 23, which can also be controlled by the control unit 9. The computed tomography system 17 further comprises an input unit 12 like a keyboard, a computer mouse, a touch pad, et cetera and a display 13 for displaying the reconstructed image.

Figure 4:
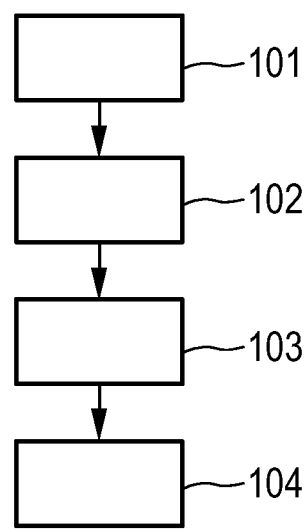
FIG. 4 shows a flowchart exemplarily illustrating an embodiment of an imaging system for generating an image of an object.

In the following an embodiment of an imaging method for generating an image of an object will exemplarily be described with reference to a flowchart shown in FIG. 4.

The imaging method for generating an image of an object is, in this embodiment, a spectral computed tomography imaging method for generating an image of a person. In step 101 the radiation source 2 rotates around the rotational axis R and the person 14 is not moved, i.e. the radiation source 2 travels along a circular trajectory around the person 14. In another embodiment, the radiation source 2 can move along another trajectory, for example, a helical trajectory, relative to the person 14. The radiation source 2 emits radiation traversing the person 14 and the radiation, which has traversed the person 14, is detected by the detector 6, which generates spectral measured projection data and non-spectral measured projection data. Step 101 can be regarded as being a projection data providing step for providing spectral measured projection data and non-spectral measured projection data.

In step 102 spectral estimated projection data 22 are estimated, which correspond to radiation paths ending at the non-spectral detection elements 15, by the estimation unit 10, wherein for estimating a spectral estimated projection data value for a radiation path ending at a non-spectral detection element 15 the estimation unit 10 a) determines a model material distribution within the imaging region 5, which could have caused a non-spectral measured projection data value that corresponds to the radiation path, based on the non-spectral measured projection data and the projection data generation parameters, and b) simulates a measurement of the spectral estimated projection data value based on the model material distribution and the projection data generation parameters. In step 103 an image of the person 14 is reconstructed based on the spectral measured projection data, the spectral estimated projection data and the projection data generation parameters, wherein in step 104 the reconstructed image is shown on the display 13.

The spectral detection elements 16 of the detector 6 are preferentially dual layer detector elements. The dual layer detector elements have two sensitive detection layers in a stack, in order to provide photon energy separation. The dual layer detector elements are well known and disclosed in, for instance, the above mentioned article by R. Carmi et al., which is herewith incorporated by reference. In other embodiments, the detector can comprise other spectral detection elements like photon counting detection elements with energy discrimination.

The production of the spectral detection elements is technically relatively complex and thus relatively expensive compared to the production of the non-spectral detection elements, which can also be regarded as being conventional detection elements. In order to reduce the complexity and thus the costs, the detector 6 is a hybrid detector, wherein a part of the detector is equipped with conventional, technically simpler and cheaper detection elements and another part is equipped with the spectral detection elements. The different parts can be asymmetrically distributed as schematically and exemplarily illustrated in FIG. 2, or they can be symmetrically distributed, wherein preferentially in each case the detector comprises a spectral inner part and two outer non-spectral parts with respect to a circumferential direction.

Besides reconstructing an image based on the spectral measured projection data and the spectral estimated projection data, the reconstruction unit 11 can also be adapted to reconstruct a conventional image, i.e. to reconstruct an image based on non-spectral projection data only, which corresponds to an image from a conventional detector and which can be reconstructed by using a standard reconstruction technique like a filtered back projection technique. In particular, the non-spectral measured projection data can be used together with spectrally integrated spectral measured projection data, which after spectral integration also form non-spectral projection data, in order to reconstruct the conventional image. If the spectral detection elements are dual layer detection elements, the readings from the two layers of a dual layer detection element may be summed, in order to generate a non-spectral projection data value.

The provided spectral measured projection data are truncated projection data, wherein the truncation could result in image artifacts in the finally reconstructed image. Especially in the case of a filtered back projection algorithm the truncated projection data can generate two problems. High frequency artifacts can be present close to the truncation boundary and low frequency components in the filtered projection data may not be correct. The image artifacts can result in a bias in the reconstructed image, wherein the bias is a substantial drawback from a clinical application point of view. Spectral computed tomography based on spectral projection data, especially dual energy computed tomography based on dual energy projection data, offers the valuable opportunity to generate quantitative clinical information like quantitative iodine maps. A bias in the reconstructed image will degrade the quantification. The computed tomography system described above with reference to FIGS. 1 and 2 allows therefore for a correction of the quantification error, especially for hybrid dual energy/conventional tomography detector systems.

The estimation unit can be adapted to estimate equivalent water lengths in the truncated regions from the conventional detection data, i.e. from the non-spectral measured projection data, and to estimate expected dual layer signals, i.e. spectral estimated projection data, from the given water lengths and known absorption characteristics of the layers of the dual layer elements. The estimated and measured dual layer signals, i.e. the measured and estimated spectral projection data, can then be combined to non-truncated projection data, which can be smoothed close to the truncation boundaries, in order to avoid sharp transitions. Then, the assembled and smoothed spectral projection data can be filtered before being back projected, in order to reconstruct the image.

In an embodiment the estimation unit is adapted to use following equation for determining a model material distribution along a radiation path that corresponds to a spectral estimated projection data value to be determined:

$$I = I_0 \int S(E) e^{-L\mu(E)} dE \qquad (1)$$

with I being the measured detection signal, i.e., for instance, the corresponding non-spectral projection data value, $I_0$ being the known detection signal without an absorbing object, E being the energy, S(E) being the known spectral response function of the entire imaging system, especially including the x-ray tube emission spectrum, a beam filtration, the spectral sensitivity function of the detector, a factor E in case of energy integrating detection elements and all other factors that influence the total energy sensitivity, L being the length of the material in the respective beam, i.e. along the respective radiation path, and μ(E) being the known linear absorption coefficient of the material. The imaging system has three different spectral response functions, i.e. a first spectral response function $S_N(E)$ for the non-spectral detection elements, a second spectral response function $S_L(E)$ for a lower layer of the spectral detection elements and a third spectral response function $S_U(E)$ for an upper layer of the spectral detection elements.

For determining an equivalent water length a non-spectral measurement $I_N$ can therefore be modeled by following equation:

$$I_N = I_0 \int S_N(E) e^{-L_{H2O} \mu_{H2O}(E)} dE, \qquad (2)$$

wherein the estimation unit can be adapted to numerically solve this equation for the equivalent water length $L_{H2O}$. In equation (2) $\mu_{H2O}$ denotes the linear absorption coefficient of water.

A spectral estimated projection data value is an energy-dependent value, i.e. for different energies or energy distributions the spectral estimated projection data value is different. For instance, it can comprise a first value $I_L$, which corresponds to the lower layer of the dual layer detector and a corresponding energy distribution detected by the lower layer, and a second value $I_U$, which corresponds to the upper layer of the dual layer detector and a corresponding energy distribution detected by the upper layer. The estimation unit can be further adapted to use the equivalent water length $L_{H2O}$ for estimating a spectral estimated projection data value consisting of $I_L$ and $I_U$, i.e. for simulating a measurement of a spectral estimated projection data value consisting of $I_L$ and $I_U$, in accordance with following equations:

$$I_L = I_0 \int S_L(E) e^{-L_{H2O} \mu_{H2O}(E)} dE \text{ and} \qquad (3)$$

$$I_U = I_0 \int S_U(E) e^{-L_{H2O} \mu_{H2O}(E)} dE. \qquad (4)$$

The estimation unit can also be adapted to reconstruct a conventional image, i.e. the intermediate image that is reconstructed based on non-spectral projection data, to segment bone areas and tissue areas within the reconstructed conventional image and to estimate calcium/water line integrals to replace a simple "water only" assumption. The estimated calcium/water line integrals can be regarded as being the spectral estimated projection data, which can be used by the reconstruction unit together with the spectral measured projection data for generating the final image.

For instance, the non-spectral intermediate image can be segmented, in order to split the image into bone and non-bone, especially soft tissue, components. For each non-spectral detection element the related material thicknesses $L_{Bone}$ for the bone component and $L_{ST}$ for the non-bone component can be determined by using the projection data generation parameters describing the radiation paths through the different segmented components, i.e. describing a forward projection of the respective segmented components. The estimation unit can then estimate the spectral projection data, i.e. simulate a measurement of the spectral projection data, in accordance with following equations:

$$I_L = I_0 \int S_L(E) e^{-L_{Bone} \mu_{Bone}(E) - L_{ST} \mu_{ST}(E)} dE \text{ and} \qquad (5)$$

$$I_U = I_0 \int S_U(E) e^{-L_{Bone} \mu_{Bone}(E) - L_{ST} \mu_{ST}(E)} dE, \qquad (6)$$

wherein in equations (5) and (6) $\mu_{Bone}$ denotes the linear bone absorption coefficient and $\mu_{ST}$ denotes the linear non-bone absorption coefficient. Since the absorption of bone is substantially similar to the absorption of calcium and the absorption of tissue is substantially similar to the absorption of water, for $\mu_{Bone}$ the linear absorption coefficient of calcium and for $\mu_{ST}$ the linear absorption coefficient of water may be used.

Although in above described embodiments the imaging system is a computed tomography system, in other embodiments the imaging system can also be another imaging system like an x-ray C-arm system.

Although in above described embodiments the imaging system is a complete imaging system comprising means for acquiring the projection data and for processing the projection data, in order to generate an image of an object, in other embodiments the imaging system can also be a system which is not adapted to acquire projection data, i.e. which does not comprise the projection data acquisition system. In this case the imaging system comprises a measured projection data providing unit for providing the measured projection data, wherein the measured projection data providing unit may just be a storing unit for storing measured projection data and for retrieving the measured projection data for providing the same, or the measured projection data providing unit may just be a receiving unit for receiving measured projection data and for providing the received measured projection data.

Although in an above described embodiment the estimation unit is adapted to estimate a water distribution, especially equivalent water lengths, which is used for estimating spectral projection data values, in other embodiments the estimation unit can be adapted to estimate other material distributions, especially other equivalent material lengths, which can be used for estimating the spectral projection data values.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the provision of the measured projection data, the estimation of the spectral estimated projection data, the smoothing of the projection data, the reconstruction of the image based on the projection data, et cetera performed by one or several units or devices can be performed by any other number of units or devices. For example, steps 102 and 103 can be performed by a single unit or by any other number of different units. These operations and/or the control of the imaging system in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging system like a computed tomography system for generating an image of an object. Spectral measured projection data and non-spectral measured projection data are generated by a detector having spectral detection elements and non-spectral detection elements, and spectral estimated projection data are estimated by using a model material distribution which could have caused the non-spectral measured projection data and by simulating a measurement of the spectral estimated projection data based on the model material distribution. An image is reconstructed based on the measured and estimated spectral projection data. Using the spectral estimated projection data in addition to the spectral measured projection data can lead to high quality spectral imaging, especially high quality spectral computed tomography imaging, which uses a simplified detector not only having generally more complex spectral detection elements, but also having simpler non-spectral detection elements.

The invention claimed is:

1. An imaging system for generating an image of an object, the imaging system comprising:
a measured projection data providing unit for providing spectral measured projection data and non-spectral measured projection data, wherein the spectral measured projection data and the non-spectral measured projection data have been generated by a detector having spectral detection elements and non-spectral detection elements, respectively, based on radiation having traversed an imaging region including the object,
an estimation unit for estimating spectral estimated projection data, which correspond to radiation paths ending at the non-spectral detection elements, wherein for estimating a spectral estimated projection data value for a radiation path ending at a non-spectral detection element the estimation unit is adapted to a) determine a model material distribution within the imaging region, which could have caused a non-spectral measured projection data value that corresponds to the radiation path, based on the non-spectral measured projection data and b) simulate a measurement of the spectral estimated projection data value based on the model material distribution,
a reconstruction unit for reconstructing an image of the object based on the spectral measured projection data and the spectral estimated projection data.

2. The imaging system as defined in claim 1, wherein for determining the model material distribution for estimating a spectral estimated projection data value the estimation unit is adapted to determine a model material distribution along a radiation path that corresponds to the spectral estimated projection data value to be determined based on a corresponding non-spectral projection data value.

3. The imaging system as defined in claim 2, wherein the estimation unit is adapted to estimate a water distribution as the model material distribution along the radiation path.

4. The imaging system as defined in claim 1, wherein for determining the model material distribution for estimating a spectral estimated projection data value the estimation unit is adapted to reconstruct an intermediate image based on the spectral measured projection data and the non-spectral projection data and to determine the material distribution based on the reconstructed intermediate image.

5. The imaging system as defined in claim 4, wherein the estimation unit is adapted to integrate the spectral measured projection data, thereby generating integrated projection data, and to reconstruct the intermediate image based on the integrated projection data and the non-spectral measured projection data.

6. The imaging system as defined in claim 4, wherein the estimation unit is adapted to determine the material distribution by segmenting different materials in the reconstructed intermediate image.

7. The imaging system as defined in claim 1, wherein the estimation unit is adapted to smooth the spectral measured and estimated projection data at a boundary between the spectral measured projection data and the spectral estimated projection data.

8. The imaging system as defined in claim 1, wherein the reconstruction unit is adapted to reconstruct the image of the object by using a filtered backprojection algorithm.

9. The imaging system as defined in claim 1, wherein the estimation unit determines an equivalent length of a given basis material along the path based on the model material distribution and the non-spectral measured projection data.

10. The imaging system as defined in claim 9, wherein the estimation unit simulates the measurement of the spectral estimated projection data value along the path based on the model material distribution and the equivalent length.

11. The imaging system as defined in claim 10, wherein the measurement of the spectral estimated projection data value includes a first spectral measurement corresponding to a first energy and a second spectral measurement corresponding to a second different energy.

12. The imaging system as defined in claim 9, wherein the estimation unit determines the equivalent length of the given basis material based on: $I_N = I_0 \int S_N(E) e^{-L\mu(E)} dE$, where $I_N$ is a measured detection signal of the non-spectral detection elements, $I_0$ is a known detection signal without an absorbing object, $S_N(E)$ is a known spectral response of the non-spectral detection elements, L is the equivalent length of the given basis material along the path, and $\mu(E)$ is a known linear absorption coefficient of the given basis material.

13. The imaging system as defined in claim 12, wherein the estimation unit simulates a first spectral measurement corresponding to a first energy based on: $I_L = I_0 \int S_L(E) e^{-L\mu(E)} dE$, where $I_L$ represents the first spectral measurement and $S_L(E)$ represents a known spectral response of first energy spectral detection elements of the spectral detection elements.

14. The imaging system as defined in claim 13, wherein the estimation unit simulates a second spectral measurement corresponding to a second different energy based on: $I_u = I_0 \int S_U(E) e^{-L\mu(E)} dE$, where $I_u$ represents the second spectral measurement and $S_U(E)$ represents a known spectral response of second energy spectral detection elements of the spectral detection elements.

15. An imaging method for generating an image of an object, the imaging method comprising:

providing spectral measured projection data and non-spectral measured projection data by a measured projection data providing unit, wherein the spectral measured projection data and the non-spectral measured projection data have been generated by a detector having spectral detection elements and non-spectral detection elements, respectively, based on radiation having traversed an imaging region including the object, estimating spectral estimated projection data, which correspond to radiation paths ending at the non-spectral detection elements, by an estimation unit, wherein for estimating a spectral estimated projection data value for a radiation path ending at a non-spectral detection element the estimation unit a) determines a model material distribution within the imaging region, which could have caused a non-spectral measured projection data value that corresponds to the radiation path, based on the non-spectral measured projection data and b) simulates a measurement of the spectral estimated projection data value based on the model material distribution, reconstructing an image of the object based on the spectral measured projection data and the spectral estimated projection data by a reconstruction unit.

16. The imaging method as defined in claim 15, wherein simulating the measurement of the spectral estimated projection data value based on the model material distribution comprises:

determining an equivalent length of a basis material along the path based on the model material distribution and the non-spectral measured projection data; and simulating the measurement of the spectral estimated projection data value based on the model material distribution, the equivalent length and the spectral measured projection data.

17. The imaging method as defined in claim 16, wherein simulating the measurement of the spectral estimated projection data value comprises:

simulating a first spectral measurement corresponding to a first energy based on the model material distribution, the equivalent length and first spectral measured projection data of the spectral measured projection data corresponding to the first energy; and simulating a second spectral measurement corresponding to a second different energy based on the model material distribution, the equivalent length and second spectral measured projection data of the spectral measured projection data corresponding to the second energy.

18. A non-transitory computer readable medium encoded with computer readable instructions of a computer program for imaging a region of interest, wherein executing the computer readable instructions with a processor causes the processor to:

provide spectral measured projection data and non-spectral measured projection data by a measured projection data providing unit, wherein the spectral measured projection data and the non-spectral measured projection data have been generated by a detector having spectral detection elements and non-spectral detection elements, respectively, based on radiation having traversed an imaging region including the object, estimate spectral estimated projection data, which correspond to radiation paths ending at the non-spectral detection elements, by an estimation unit, wherein for estimating a spectral estimated projection data value for a radiation path ending at a non-spectral detection element the estimation unit a) determines a model material distribution within the imaging region, which could have caused a non-spectral measured projection data value that corresponds to the radiation path, based on the non-spectral measured projection data and b) simulates a measurement of the spectral estimated projection data value based on the model material distribution, and reconstruct an image of the object based on the spectral measured projection data and the spectral estimated projection data by a reconstruction unit.

19. The non-transitory computer readable medium as defined in claim 18, wherein executing the computer readable instructions with the processor further causes the processor to:

determine an equivalent length of a basis material along the path based on the model material distribution and the non-spectral measured projection data; and simulate the measurement of the spectral estimated projection data value based on the model material distribution, the equivalent length and the spectral measured projection data.

20. The non-transitory computer readable medium as defined in claim 19, wherein executing the computer readable instructions with the processor further causes the processor to:

simulate a first spectral measurement corresponding to a first energy based on the model material distribution, the equivalent length and first spectral measured projection data of the spectral measured projection data corresponding to the first energy; and simulate a second spectral measurement corresponding to a second different energy based on the model material distribution, the equivalent length and second spectral measured projection data of the spectral measured projection data corresponding to the second energy.

* * * * *